United States Patent [19]

Fox et al.

[11] Patent Number: 4,533,775

[45] Date of Patent: Aug. 6, 1985

[54] PROCESS FOR THE UPGRADING OF LOWER ALCOHOLS TO HIGHER MOLECULAR WEIGHT ALCOHOLS

[75] Inventors: Joseph R. Fox, Solon; Frederick A. Pesa, Aurora; Benedict S. Curatolo, Maple Heights, all of Ohio

[73] Assignee: The Standard Oil Company, Cleveland, Ohio

[21] Appl. No.: 488,286

[22] Filed: Apr. 25, 1983

[51] Int. Cl.³ .............................................. C07C 29/34
[52] U.S. Cl. ...................................... 568/905; 252/373; 423/415 A; 423/648 R; 585/733
[58] Field of Search ..................... 568/905, 851, 922

[56] References Cited

U.S. PATENT DOCUMENTS

| | | | |
|---|---|---|---|
| 2,451,945 | 10/1948 | Hanford | 568/851 |
| 3,009,964 | 11/1961 | Russell | 568/851 |
| 3,328,470 | 6/1967 | Poe | 568/905 |
| 3,341,606 | 9/1967 | Mottern | 568/851 |
| 3,358,041 | 12/1967 | Mottern et al. | 568/851 |
| 3,864,407 | 2/1975 | Yates | 568/905 |

FOREIGN PATENT DOCUMENTS 335631 10/1930 United Kingdom ............... 568/905

*Primary Examiner*—J. E. Evans
*Attorney, Agent, or Firm*—Teresan W. Gilbert; Joseph G. Curatolo; Larry W. Evans

[57] ABSTRACT

A process is provided for the upgrading of lower alcohols to higher molecular weight alcohols by contacting the lower alcohol with a reaction promoter composition selected from alkali metal acetylides, Group IB metal acetylides, acetylides of the naturally occurring lanthanide and actinide series metals, rare earth metal hydrides, alkaline earth metal hydrides and alkoxides and alkali metal alkoxides.

9 Claims, No Drawings

PROCESS FOR THE UPGRADING OF LOWER ALCOHOLS TO HIGHER MOLECULAR WEIGHT ALCOHOLS

BACKGROUND OF THE INVENTION

The process of the present invention relates to the upgrading of lower alcohols to form higher molecular weight alcohols. More particularly, the process of the present invention relates to the contacting of lower molecular weight alcohols such as methanol, ethanol and propanol with a solid reaction promoter composition to form alcohols having higher molecular weight, i.e. a greater number of carbon atoms per molecule.

Lower alcohols are easily produced by a variety of methods. Methanol is produced from natural gas or coal partially oxidized to form carbon monoxide and hydrogen, followed by catalytic conversion to methanol. Ethanol and propanol can be produced by direct hydration of ethylene and propylene, respectively. Ethanol can also be formed by the fermentation of sugars.

Methods have been sought for the production of higher molecular weight alcohols from lower alcohols. The higher molecular weight alcohols are useful as solvents, fuels, gasoline extenders, and intermediates for other chemical products.

It has been shown that the homologation of lower alcohols such as methanol can be carried out in the liquid phase under high pressure with the introduction of synthesis gas, or carbon monoxide and hydrogen, in the presence of a Group VIII catalyst such as cobalt, nickel, and ruthenium. Variations of this process are described in U.S. Pat. Nos. 3,248,432; 3,285,948; 3,387,043; 4,126,752; 4,133,966; 4,150,246; 4,168,391; 4,233,466; 4,205,190; 4,111,837; 4,171,461 and 4,239,925. These processes generally require the presence of a corrosive promoter such as iodide compounds.

In the 1940's, Yogryoji Negishi investigated the formation of butyl alcohols in the presence of calcium carbide. In one set of experiments, mixtures of carbon monoxide and hydrogen were contacted in the presence of a methanol catalyst and calcium carbide to form butanol. In another set of experiments, ethanol and hydrogen were contacted with a paste consisting of 100 grams of calcium carbide, 400 grams of carbonate or calcium oxide, and 1,000 grams of a paste vehicle such as lubricating oil to result in the isolation of butanol, and possibly hexanol.

U.S. Pat. No. 3,972,952 describes the vapor phase conversion of methanol and ethanol to higher linear primary alcohols by heterogeneous catalysis. The catalyst composition utilized was made up of particles of an inert, high surface area support such aluminum oxide, impregnated with inorganic base promoters such as oxides, hydroxides, or basic salts of alkali metals or alkaline earth metals, and a platinum group metal. The process was carried out in the presence of synthesis gas at elevated pressure.

It is therefore an object of the invention to upgrade lower alcohols, particularly methanol, to form higher molecular weight alcohols.

SUMMARY OF THE INVENTION

The process of the present invention provides a method for the upgrading of lower alcohols to higher molecular weight alcohols (alcohols having a greater number of carbon atoms than the initially reacted lower weight alcohols), most effectively in the vapor phase, and in the presence of a solid reaction promoter compound. In the process of the present invention, carbon monoxide and hydrogen are not required to be co-fed with the lower molecular weight alcohol in order to induce alcohol "homologation", and the process of the present invention can be carried out in the absence of co-fed carbon monoxide and/or hydrogen. Further, the process of present invention can be carried out at relatively low reaction pressure, and preferably is carried out at atmospheric pressure. Corrosive promoters are not required in the process of the present invention.

The present invention includes a process for the upgrading of lower alcohols, selected from methanol, ethanol, and propanol, comprising contacting at least one lower alcohol with a reaction promoter composition at a temperature of about 25° C. to about 600° C., wherein said promoter composition is selected from:

(a) A metal acetylide represented by the formula $$Ma_2C_2 \qquad (I)$$

wherein Ma is selected from Li, Na, K, Rb, Cs, Cu, Ag, Au and mixtures thereof; or $$MeC_2 \qquad (II)$$

wherein Me is selected from La, Ce, Pr, Nd, Sm, Eu, Gd, Tb, Dy, Ho, Er, Tm, Yb, Lu, Ac, Th, Pa, U, and mixtures thereof;

(b) A hydride of a metal selected from Mg, Ca, La, Ce, Pr, Nd, Sm, Eu, Gd, Tb, Dy, Ho, Er, Tm, Yb, Lu and mixtures thereof;

(c) A $C_1$ to $C_3$ alkoxide of a metal selected from Li, Na, K, Rb, Cs, Mg, Ca, Ba, Sr and mixtures thereof; and, (d) A mixture of reaction promoter compositions of groups (a), (b), and (c).

DETAILED DESCRIPTION OF THE INVENTION

Reaction Composition

The alcohols which are upgraded according to the process of the present invention include methanol, ethanol, and propanol. Methanol is the preferred feedstock, which can be converted into higher molecular weight alcohol products having generally from two carbon atoms to about seven carbon atoms. Products of this reaction include ethanol, propanol, n-butanol, isobutanol, 2-methyl-1-butanol and 2-methyl-1-pentanol. Isobutanol is the predominant product when methanol is converted in the inventive process. The upgrading of ethanol according to the inventive process generally yields n-butanol as the major alcohol product.

Compositions suitable for promoting the alcohol upgrading reaction include metal acetylides, or carbides, particularly alkali metal acetylides, Group IB metal acetylides, and acetylides of the naturally occurring lanthanide metal series and actinide metal series. Preferred acetylide reaction promoter compositions include $Na_2C_2$, $LaC_2$ and $CeC_2$. These acetylides are commercially available, for example, from Alfa Products, Ventron Division of Thiokol (Danvers, Mass.) or may be produced by the carbothermic reduction of the corresponding metal or metal oxide. Care must be exercised when using acetylides as $ThC_2$, which is pyrophoric.

Other reaction promoter compositions include alkaline earth metal and rare earth metal hydrides, preferably $CaH_2$ and $CeH_3$, available from Alfa Products or Fisher Scientific (Pittsburgh, Pa.) and alkali metal or alkaline earth metal alkoxides (methoxides, ethoxides, propoxides), preferably $NaOCH_3$ and $Ca(OCH_3)_2$, available from Alfa Products or Fluka Chemical Corp. (Hauppauge, N.Y.) or produced by the liquid phase reaction of the metal or metal hydride with the corresponding alcohol.

Reaction Conditions

While the process of the present invention may be carried out in the liquid phase, the process is most preferably carried out in the vapor phase. The gaseous lower alcohol is contacted with the solid reaction promoter composition at a reaction temperature of 25° C. to about 600° C., preferably 200° C. to about 500° C. and most preferably 300° C. to about 450° C. The reaction can be conducted at atmospheric pressure, but reaction at elevated pressure is not deleterious to the reaction. Reaction pressure therefore generally may fall within the range of about 1 to about 300 atmospheres, preferably about 1 to about 100 atmospheres. The reaction can be carried out in a fixed or fluid bed reactor, charged with the reaction promoter composition. Conversion can be increased by recycle of effluents to the reactor, before or after separation of the higher alcohol product, preferably, after.

The lower alcohol may be introduced into the reaction in the presence of an inert carrier gas such as nitrogen, helium or the like. Although carbon monoxide and hydrogen are not deleterious to the alcohol upgrading reaction, and may be introduced into the reaction zone, the process of the present invention does not require that carbon monoxide or hydrogen be introduced with the alcohol in order for the upgrading reaction to proceed.

In addition to the higher molecular weight alcohol product, in the upgrading process of the present invention gaseous hydrocarbons are also formed, including ethane, ethylene, acetylene and propane, suitable for use as fuels or chemical feedstocks. By-products of the reaction include hydrogen, carbon monoxide, carbon dioxide and methane. Also, at high temperatures, about 500° C., the formation of esters, such as methyl formate, is observed.

The contact time of the lower alcohol with the reaction promoter composition may generally be about 0.1 seconds to about 100 seconds, preferably 0.5 seconds to about 25 seconds. An increase in contact time generally results in an increase in the molecular weight of the product alcohols, accompanied however, by an increase in methane production.

SPECIFIC EMBODIMENTS

The examples below were performed according to the following procedure. The reaction promoter composition was supported on a porous frit inside a fused quartz tube reacter 18 inches in length, and having internal diameter of 20 mm and an outer diameter of 23.6 mm. The reactor was heated inside a vertically mounted electric furnace.

The lower alcohol reactant was delivered to the reactor at a set flow rate of 0.05–0.1 ml per minute, and was vaporized prior to entering the reactor. The alcohol was passed upward through the catalyst bed in the presence of a helium carrier gas, at a helium flow rate of about 10–40 ml per minute.

Liquid products were collected in an ice-cooled trap and analyzed by gas chromatography. The effluent gas was collected and analyzed also by gas chromatography.

EXAMPLE 1

$CeC_2$ (5 g) was heated in the reactor to 200° C. under a helium flow of 10 ml per minute. Methanol was fed into the system at a flow rate of 0.1 ml per minute, and was vaporized prior to entering the reactor. The reaction temperature was maintained at 200° C. for 25 minutes, increased to 300° C. for 25 minutes and further increased to 400° C. for 25 minutes. The liquid and gaseous products were collected and are reported in Table I below.

TABLE I

| Liquid Products | Weight Percent |
| --- | --- |
| methanol | 77.4893 |
| ethanol | 0.1071 |
| isopropanol | 0.0418 |
| propanol | 0.0941 |
| isobutanol | 3.0533 |
| 2-methyl-1-butanol | 0.3654 |
| 2-methyl-1-pentanol | 0.2002 |
| Water constitutes the bulk of the rest of the liquid mixture. | |

| Gaseous Products | Mole Percent |
| --- | --- |
| $H_2$ | 38.1569 |
| CO | 14.7032 |
| $CH_4$ | 10.6141 |
| $C_2H_2$ | 0.9133 |
| $C_2H_6$ | 0.2798 |
| $C_2H_4$ | 0.4064 |
| $CO_2$ | 0.0276 |
| $C_3H_8$ | 0.0808 |
| The other major component of the gas phase was the carrier gas He. | |

EXAMPLE 2

Ten grams of $CeC_2$ were charged to the reactor and heated under a helium flow of 10 ml per minute to a temperature of 400° C. Methanol was introduced into the system at a flow rate of 0.1 ml per minute and vaporized. Products collected after a reaction time of 32 minutes are reported in Tables II through IV.

EXAMPLE 3

The reaction procedure of Example 2 was followed, utilizing 10 grams of $LaC_2$ as the reaction promoter compound. The product sample collected after a reaction time of 37 minutes is reported in Tables II through IV.

EXAMPLE 4

The reaction procedure of Example 2 was followed, charging 5 grams $Na_2C_2$ to the reactor. The product sample collected after 46 minutes reaction time is reported in Tables II through IV.

Table II reports weight percentage of liquid products, Table III reports selectivity to higher alcohols, and Table IV reports the mole percentage of gaseous products.

The abbreviations used in the Tables stand for the following compounds:

| List of Abbreviations | |
|---|---|
| MEOH | Methanol |
| ETOH | Ethanol |
| PROH | Propanol |
| i-BUOH | iso-Butanol |
| BUOH | n-Butanol |
| 2-MeBUOH | 2-Methyl-1-butanol |
| 2-MeC5OH | 2-Methyl-1-pentanol |

Definition of Selectivity

Selectivity is defined as $$\frac{\text{number of moles } C_{alcohol}}{\text{number of moles } C_{higher\ alcohol}} \times 100 \text{ percent}$$

where "moles C" represents the number of moles of a particular alcohol in a given liquid sample multiplied by the number of carbon atoms in the molecule.

TABLE II

Liquid Product Distribution for Metal Acetylides as Reaction Promoter Compositions

| Example No. | Metal Acetylide | Contact Time (Sec.) | Reaction Time (min) | Weight Percent | | | | | | |
|---|---|---|---|---|---|---|---|---|---|---|
| | | | | MEOH | ETOH | PROH | i-BUOH | BUOH | 2-Me BUOH | 2-Me C5OH |
| 2 | CeC2 | 1.6 | 32 | 92.66 | 0.12 | — | 1.85 | — | 0.55 | 0.11 |
| 3 | LaC2 | 1.6 | 37 | 86.46 | 0.14 | 0.08 | 1.89 | — | 0.46 | — |
| 4 | Na2C2 | 4.9 | 46 | 78.31 | 0.31 | 0.51 | 1.36 | 0.08 | 0.38 | — |

TABLE III

Higher Alcohol Selectivity

| Example No. | Metal Acetylide | ETOH | PROH | i-BUOH | BUOH | 2-Me BUOH | 2-Me C5OH |
|---|---|---|---|---|---|---|---|
| 2 | CeC2 | 9.6 | 5.2 | 67.7 | — | 12.1 | 0.8 |
| 3 | LaC2 | 10.2 | 8.0 | 67.2 | 3.2 | 10.0 | — |
| 4 | Na2C2 | 19.8 | 22.4 | 43.4 | 5.7 | 6.2 | — |

TABLE IV

Gaseous Product Distributions for Metal Acetylides as Reaction Promoter Compositions[a]

| Example No. | Metal Acetylide | Mole Percent | | | | | | |
|---|---|---|---|---|---|---|---|---|
| | | CO | H2 | CH4 | C2H6 | C2H4 | C2H2 | CO2 |
| 2 | CeC2 | 15.82 | 41.27 | 13.79 | 0.26 | 0.19 | 0.06 | 0.18 |
| 3 | LaC2 | 17.63 | 41.41 | 3.28 | 0.18 | 0.18 | 0.11 | 0.11 |
| 4 | Na2C2 | 1.86 | 61.76 | 2.25 | 0.36 | 0.17 | — | 0.14 |

[a]The remainder of the sample consists of the carrier gas helium and O2 and N2 impurities from sampling.

EXAMPLE 5

In order to determine whether the carbon atoms which were being incorporated into the higher alcohol chain were being derived from the reactant lower alcohol, as opposed to being derived from the carbon present in the metal acetylides, carbon 13-labelled methanol (99 percent carbon 13) was reacted according to the process of the present invention. $^{13}CH_3OH$ was fed into the reactor containing 10 grams of $CeC_2$ at a flow rate of 0.1 ml per minute for 30 minutes at 400° C. (utilizing a helium carrier gas with a flow rate of about 10 ml per minute). The helium carrier gas was further used to flush the system for an additional 10 minutes.

A combination of gas chromatography/mass spectroscopy and gas chromatography/infra-red spectroscopy was used to analyze the higher alcohol and gaseous products. The mass spectrum of isobutanol indicated that the parent ion had undergone a shift of 4 mass units from 74 to 78 amu when carbon 13-labelled methanol was used as the feed. This increase in mass can only be due to the incorporation of 4 carbon 13 atoms from the carbon 13-labelled methanol and thus clearly demonstrates that the lower alcohol and not the carbon contained in the metal acetylide is the source of the higher alcohols. Analysis of the 2-methyl-1-butanol and 2-methyl-1-pentanol from the carbon 13-methanol reaction showed analogous increases of 5 and 6 mass units for the parent ion respectively.

The gaseous products from the carbon 13-methanol upgrading reaction were studied by high resolution infra-red spectroscopy. The carbon monoxide and methane by-products in the gas phase contained essentially no carbon 12, demonstrating that the metal acetylide was not contributing carbon to the product, but rather that the lower alcohol is the source of the product carbon compounds.

EXAMPLE 6

The reaction procedure of example 2 was repeated in the presence of $CeC_2$ utilizing $CH_3OD$ as the lower alcohol. The liquid product mixture was analyzed by gas chromatography/infra-red spectroscopy and nuclear magnetic resonance spectroscopy. In the GC/IR spectrum of isobutanol, in addition to the —OH and —CH stretches at about 3,700 cm$^{-1}$ and about 2,900 cm$^{-1}$ respectively, the spectrum clearly indicated an —OD stretch at about 2,800 cm$^{-1}$ and a —CD stretch at about 2,200 cm$^{-1}$. The appearance of the last band indicates that deuterium incorporation has occurred somewhere in the carbon backbone of the isobutanol. NMR analysis indicated resonances which are attributed to deuterium present in methyl, methylene, and methine groups, further indicating that deuterium incorporation has occurred throughout the higher alcohols which are formed from $CH_3OD$. Gas chromatography/mass spectroscopy analysis of the gaseous products indicated that significant deuterium incorporation into methane hydrogen has also occurred.

EXAMPLE 7

The reaction procedure of Example 1 was repeated, except that ethanol was used as the lower alcohol reactant. The predominant alcohol formed was n-butanol with lesser amounts of isopropyl alcohol, propanol, isobutanol, 2-methyl-1-pentanol and 1-hexanol also being produced. A significant amount of ethylene was produced in the reaction.

EXAMPLE 8

The reaction procedure of Example 2 was repeated, except that 10 grams $CaH_2$ was utilized as the reaction promoter composition for the upgrading of methanol. Product samples were taken after 1 hour reaction time and 2 hours reaction time. The reaction products are reported in Table V.

TABLE V

| | Higher Alcohols using $CaH_2$ as the Reaction Promoter Composition Weight Percent | | | | | Gaseous Products Using $CaH_2$ as the Reaction Promoter Composition Mole Percent | | | | |
|---|---|---|---|---|---|---|---|---|---|---|
| Run Time (h) | MEOH | ETOH | PROH | i-BuOH | 2-Me-BuOH | $H_2$ | $C_2H_4$ | $C_2H_6$ | $CH_4$ | CO |
| 1 | 93.73 | 0.24 | 0.17 | 4.38 | 0.41 | 49.8 | 0.8 | 0.3 | 22.8 | 5.4 |
| 2 | 98.32 | 0.26 | 0.05 | 1.04 | 0.12 | 39.2 | 0.3 | 0.2 | 19.0 | 7.6 |

The remainder is helium carrier gas and $O_2$ and $N_2$ impurities from sampling procedure.

The reaction procedure of Example 8 was repeated utilizing calcium carbonate, calcium oxide, and calcium hydroxide as the reaction promoter composition. No higher molecular weight alcohol production was detected when these compounds were tested as reaction promoter compositions.

EXAMPLE 9

Fifteen grams of $NaOCH_3$ was loaded into the reactor and was heated under helium at a flow rate of 35 milliliters per minute to a temperature of 300° C. Methanol was introduced into the system at a flow rate of 0.1 ml per minute and vaporized before entering the reactor for a reaction run time of 45 minutes. A liquid product sample was taken and analyzed to exhibit the higher molecular weight alcohol products reported in Table VI.

TABLE VI

| Liquid Products | Weight Percent |
|---|---|
| methanol (unreacted) | 65.6 |
| ethanol | 0.77 |
| propanol | 2.9 |
| isopropanol | 3.3 |
| isobutanol | 17.8 |
| 2-methyl-l-butanol | 1.2 |
| 2-methyl-l-pentanol | 0.66 |
| Gaseous Products | Mole Percent |
| hydrogen | 38.4 |
| ethylene | 0.1 |
| ethane | 0.2 |
| methane | 1.2 |
| carbon monoxide | 0.2 |

The remainder is helium carrier gas and $O_2$ and $N_2$ impurities from sampling procedure.

Sodium carbonate was tested as a reaction promoter composition for the upgrading of methanol, but no higher alcohol products were detected.

EXAMPLE 10

The reaction procedure of Example 2 was followed, utilizing 10 g uranium acetylide (from Cerac Incorporated) as the reaction promoter composition. Liquid products included 0.19 weight percent ethanol and 0.13 weight percent iso-butanol. Gaseous products included hydrogen: 22.8 mole percent, $CO_2$:0.6 mole percent, CO:13.0 mole percent and methane:15.7 mole percent.

Thus it should be apparent to those skilled in the art that the subject invention accomplishes the objects set forth above. Although conversions of lower alcohol may appear low, such conversions may be increased by utilization of larger reactors containing a deeper bed of reaction promoter compositions, increasing contact times and the like. It is to be understood that the subject invention is not to be limited by the examples set forth herein. These have been provided merely to demonstrate operability, and the selection of reaction promoter compositions and reaction conditions can be determined from the total specification disclosure provided without departing from the spirit of the invention herein disclosed and described, the scope of the invention including equivalent embodiments, modifications and variations that fall within the scope of the attached claims.

We claim:

1. A process for the upgrading of methanol to substantially isobutanol and other higher molecular weight alcohol products comprising contacting methanol in the vapor phase with a reaction promoter composition at a reaction temperature of about 25° C. to about 600° C., wherein said promoter composition is selected from:

(a) A metal acetylide represented by the formula $$Ma_2C_2 \qquad (I)$$

wherein Ma is selected from Li, Na, K, Rb, Cs, Cu, Ag, Au and mixtures thereof; or $$MeC_2 \qquad (II)$$

wherein Me is selected from La, Ce, Pr, Nd, Sm, Eu, Gd, Tb, Dy, Ho, Er, Tm, Yb, Lu, Ac, Th, Pa, U, and mixtures thereof;

(b) A hydride of a metal selected from Mg, Ca, La, Ce, Pr, Nd, Sm, Eu, Gd, Tb, Dy, Ho, Er, Tm, Yb, Lu and mixtures thereof; and (c) A mixture of reaction promoter compositions of groups (a) and (b).

2. A process as in claim 1 wherein said methanol is contacted with the reaction promoter composition at a reaction pressure of about 1 to about 300 atmospheres.

3. A process as in claim 1 wherein said methanol is contacted with the reaction promoter composition at a reaction pressure of about 1 to about 100 atmospheres.

4. A process as in claim 1 wherein said methanol is contacted with the reaction promoter composition in the absence of co-fed carbon monoxide or hydrogen.

5. A process as in claim 1 wherein, in the reaction promoter composition of formula I, Ma is sodium.

6. A process as in claim 1 wherein, in the reaction promoter composition of formula II, Me is cerium.

7. A process as in claim 1 wherein, in the reaction promoter composition of formula II, Me is lanthanum.

8. A process as in claim 1 wherein, in the reaction promoter composition of formula II, Me is uranium.

9. A process as in claim 1 wherein the reaction promoter composition is calcium hydride.

* * * * *